United States Patent
Chung et al.

(10) Patent No.: US 8,057,672 B2
(45) Date of Patent: Nov. 15, 2011

(54) DISPOSABLE MULTI-LAYERED FILTRATION DEVICE FOR THE SEPARATION OF BLOOD PLASMA

(75) Inventors: Kwang Hyo Chung, Daejeon (KR); Yo Han Choi, Daejeon (KR); Dae Sik Lee, Daejeon (KR); Ju Hyun Jeon, Daejeon (KR); Moon Youn Jung, Daejeon (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 744 days.

(21) Appl. No.: 12/133,295

(22) Filed: Jun. 4, 2008

(65) Prior Publication Data

US 2009/0120865 A1    May 14, 2009

(30) Foreign Application Priority Data

Nov. 13, 2007    (KR) .................. 10-2007-0115663

(51) Int. Cl.
*B01D 69/06*    (2006.01)
*B01D 63/08*    (2006.01)
*B01D 29/00*    (2006.01)

(52) U.S. Cl. .......... 210/321.84; 210/252; 210/257.1; 210/321.6; 210/321.75; 210/348; 210/433.1; 210/436; 210/446; 210/453; 210/472; 210/477; 210/482; 210/483; 210/484; 210/485; 210/488; 210/489; 210/490; 210/491; 210/497.01; 210/498; 210/500.22; 210/500.26; 210/500.27; 210/500.29; 210/504; 210/505; 210/506; 210/508

(58) Field of Classification Search .............. 210/252, 210/257.1, 257.2, 321.6, 321.75, 321.84, 210/348, 433.1, 436, 446, 453, 472, 477, 210/482, 483, 484, 485, 488, 489, 490, 491, 210/497.01, 498, 500.22, 500.26, 500.27, 210/500.29, 503, 504, 505, 506, 507, 508; 422/55, 57, 58, 59, 60, 61, 73, 82.01, 82.05, 422/82.09, 99, 101, 102, 104

See application file for complete search history.

(56) References Cited

U.S. PATENT DOCUMENTS

| 3,747,769 A | * | 7/1973 | Brumfield | 210/350 |
| 4,923,620 A | * | 5/1990 | Pall | 210/767 |
| 5,711,871 A | * | 1/1998 | Miltenyi | 210/86 |
| 6,008,040 A | * | 12/1999 | Datar | 435/325 |

(Continued)

FOREIGN PATENT DOCUMENTS

KR    10-2005-0075431 A    7/2005

(Continued)

OTHER PUBLICATIONS

Timothy A. Crowley et al., "Isolation of plasma from whole blood using planar microfilters for lab-on-a-chip applications", The Royal Society of Chemistry 2005, Lab on a Chip, pp. 922-929, vol. 5, No. 9.

*Primary Examiner* — John Kim

(57) ABSTRACT

Provided is a disposable multi-layered filtration device for the separation of blood plasma which can be applied to a biochip and appropriate for disposal uses. The filtration device for the separation of blood plasma includes: an upper substrate including a blood inlet; an intermediate substrate including a filtering unit for extracting blood plasma from blood flowing through the blood inlet; and a lower substrate including an air outlet, wherein the upper substrate, the intermediate substrate, and the lower substrate are stacked and adhered.

14 Claims, 5 Drawing Sheets

U.S. PATENT DOCUMENTS

| | | | |
|---|---|---|---|
| 6,168,718 B1 * | 1/2001 | Sutter et al. | 210/651 |
| 2006/0029923 A1 | 2/2006 | Togawa et al. | |
| 2006/0165558 A1 * | 7/2006 | Witty et al. | 422/58 |
| 2008/0047892 A1 | 2/2008 | Kim et al. | |
| 2008/0289692 A1 * | 11/2008 | Zucchelli et al. | 137/2 |

FOREIGN PATENT DOCUMENTS

| | | |
|---|---|---|
| KR | 100577367 B1 | 4/2006 |
| WO | WO99/58172 | 11/1999 |
| WO | WO2004-046716 A1 | 6/2004 |
| WO | WO2004-084974 A1 | 10/2004 |

* cited by examiner

DISPOSABLE MULTI-LAYERED FILTRATION DEVICE FOR THE SEPARATION OF BLOOD PLASMA

CROSS-REFERENCE TO RELATED APPLICATIONS

This application claims the priority of Korean Patent Application No. 10-2007-0115663 filed on Nov. 13, 2007, in the Korean Intellectual Property Office, the disclosure of which is incorporated herein by reference.

BACKGROUND OF THE INVENTION

1. Field of the Invention

The present invention relates to a filtration device for the separation of blood plasma used to separate blood plasma from whole blood, and more particularly, to a disposable multi-layered filtration device for the separation of blood plasma which can be applied to a biochip.

The present invention was supported by the IT R&D Program of MIC/IITA [2006-S-007-02, Ubiquitous Health Management Module/System].

2. Description of the Related Art

Blood circulates around the body through blood vessels of a person or an animal. The blood has various functions of supplying oxygen inhaled via lungs to tissues, carrying carbon dioxide from the tissues to the lungs to be exhaled, supplying nutrients absorbed by the digestive organs to other organs or the tissues, transporting a waste product of metabolism produced by cells to the kidney so that the kidney secretes the waste product into the urine, transporting hormones produced by the endocrine glands to corresponding organs and tissues, transporting heat through the body to regulate the body temperature, attacking and detoxifying infections agents and foreign substances, and the like.

Blood is used as an important indicator for diagnosing diseases or health states. Particularly, a protein chip is a kind of biochip for detecting or measuring an expression of a specific protein or an amount of a specific protein in a blood sample to diagnose diseases associated with the protein and manages convalescence.

Blood is composed of a liquid called blood plasma and blood cells suspended within the plasma. The blood plasma is predominantly water containing dissolved proteins, glucoses, fatty acids, minerals, and other substances, and the blood cells present in blood are red blood cells, white blood cells, and platelets. Since the protein to be detected generally presents in blood plasma, a protein chip needs a filter element for separating only blood plasma from blood in order to obtain quantitative results with high sensitivity.

A general blood filter is used to process rapidly a large amount of blood. However, a blood filter of the protein chip requires fast separation using a small amount of blood without contamination of blood plasma.

As existing methods introduced to separate blood plasma from whole blood, there are a method of separating blood cells and blood plasma from each other by using centrifugal force, a method of disposing a microstructure having a size smaller than blood cells at a flowpath and pumping blood so that blood cells are filtered out and only blood plasma is remained, a method of disposing a diaphragm having a small height so as not to enable blood cells to pass through but to enable blood plasma to pass through the diaphragm, a method of disposing a paper, a glass fiber, a porous medium, or a membrane at a side or front surface of flows of blood to separate blood cells, a method of using sedimentation effects of blood cells caused by gravity so that blood cells and blood plasma are layered so that the blood plasma can be extracted, a method of applying an electrical signal to deflect flows of blood cells, and the like.

Specifically, as an example, PCT International Publication No. WO2004/084974 (titled "BLOOD FILTER DEVICE AND METHOD OF PRODUCING THE SAME", published on Oct. 7, 2004) discloses a blood filter device which has a flow inlet formed at a side surface of a dome portion horizontally so that blood flowing through the flow inlet into the dome portion passes through a filter and flows out through an outlet and impurities, thrombus, and the like in the blood are removed to remain only blood plasma. Here, air bubbles in the blood can be easily removed through an air outlet provided in the top of the dome portion.

As another example, PCT International Publication No. WO2004/046716 (titled "PLASMA OR SERUM SEPARATION MEMBRANE AND FILTER APPARATUS INCLUDING THE PLASMA OR SERUM SEPARATION MEMBRANE", published on Jun. 3, 2004) discloses a filter apparatus which has a tube-shaped member including a filter member provided at the top portion of the tube-shaped member. After the tube-shaped member is sealed and fixed, the tube-shaped member is decompressed so that blood collected in the tube-shaped member is filtered to separate blood plasma or serum.

As another example, PCT International Publication No. WO99/058172 (titled "FILTER DEVICE AND METHOD FOR PROCESSING BLOOD", published on Nov. 18, 1999) discloses a filter device for processing blood to effectively remove specific components from a large amount of blood. In the filter device, a blood filter layer and a space layer on a sheet where blood flows more easily through the spacer layer than through the filter layer are stacked and coiled, and an end portion of the spacer layer on the sheet is exposed to an outer circumference of a filter member, so that several liters of blood are processed and desired target materials can be easily removed.

However, most of the existing blood filters are used to process a large amount of blood and cannot be implemented as chips.

In addition, existing blood filter devices have structures including filter members such as papers, glass fibers, membranes, porous media, and the like, so that manufacturing processes are complex and high manufacturing costs are required, and the filter devices are not appropriate for disposable uses.

In addition, the existing blood filter devices have problems such as blocked flow paths, decreases in blood plasma separation efficiency, increases in separation time, and complex operations, and the like, due to structural characteristics.

SUMMARY OF THE INVENTION

An aspect of the present invention provides a disposable multi-layered filtration device for the separation of blood plasma which is appropriate for disposable uses, can be easily manufactured, has a simple structure, and can be directly applied to a biochip.

An aspect of the present invention also provides a disposable multi-layered filtration device for the separation of blood plasma which can separate blood plasma with a simple operation of injecting blood and pressing the filter device without an additional unit.

An aspect of the present invention also provides a disposable multi-layered filtration device for the separation of blood plasma which can separate rapidly blood plasma from a small amount of blood and has high blood plasma separation efficiency.

According to an aspect of the present invention, there is provided a disposable multi-layered filtration device for the separation of blood plasma, including: an upper substrate including a blood inlet; an intermediate substrate including a filtering unit for extracting blood plasma from blood flowing through the blood inlet; and a lower substrate including an air outlet, wherein the upper substrate, the intermediate substrate, and the lower substrate are stacked and adhered.

In the above aspect of the present invention, the filtering unit may include: a filter chamber which is formed by perforating the intermediate substrate in a direction of a thickness of the intermediate substrate at a position facing the blood inlet and includes one or more filters for filtering the blood flowing from the blood inlet to pass only the blood plasma; a microchamber that the blood plasma extracted by the filter of the filter chamber fills; and a microchannel connecting the filter chamber to the microchamber. Here, the filter may be made of a paper, a glass fiber, or a porous material.

In addition, the microchamber may further include one or more of antigens, antibodies, enzymes, micro/nano particles, electrodes, and sensors for generating biological reactions and detections with the blood plasma filling the microchamber.

In addition, the filter chamber may further include a lower elastic plate which is disposed at a lower portion of the filter, has a shape of O, and has an opening portion for enabling the blood plasma to flow into the microchannel. In addition, the filter chamber may further include an upper elastic plate which is disposed at an upper portion of the filter and has the shape of O. Here, a thickness of the filter chamber may be equal to or less than the sum of thicknesses of the filters and the upper and lower elastic plates so that the filters and the upper and lower elastic plates are pressed in the filter chamber by the adhered upper, intermediate, and lower substrates.

In addition, the disposable multi-layered filtration device for the separation of blood plasma may further include an adhesive means and a cover film for sealing the blood inlet. In addition, the cover film may be made of a thin polymer film so that the cover film is deformed when pressed and maintains the deformed shape after the pressing is removed. In addition, the adhesive means may be a double sided adhesive tape formed in a shape of a closed curve at an upper boundary of the blood inlet so as to be adhered to the cover film and the upper substrate.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Exemplary embodiments of the present invention will now be described in detail with reference to the accompanying drawings.

Figure 1:
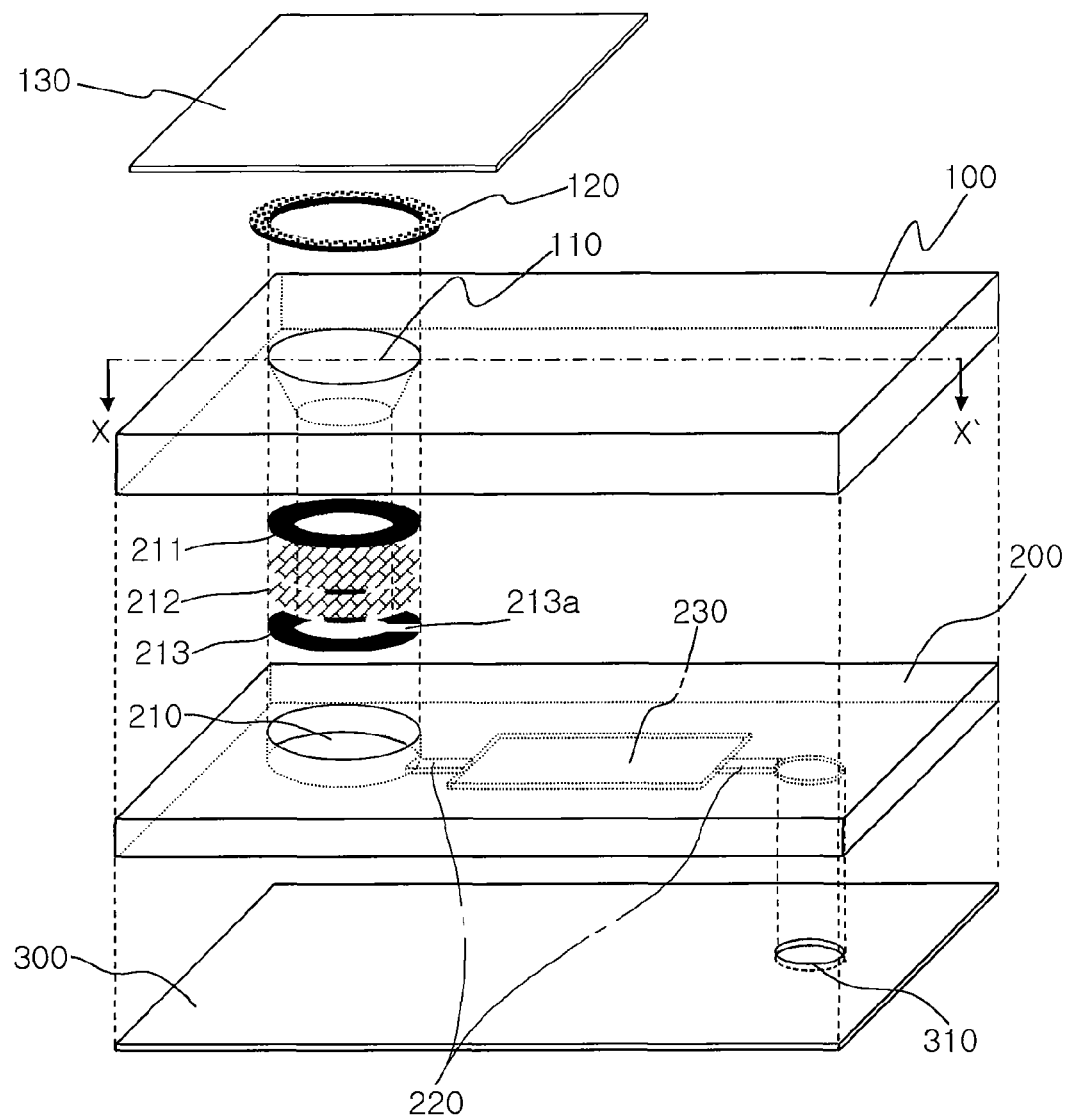
FIG. 1 is a perspective exploded view for explaining a filtration device for separating blood plasma according to an embodiment of the present invention.
Figure 2:
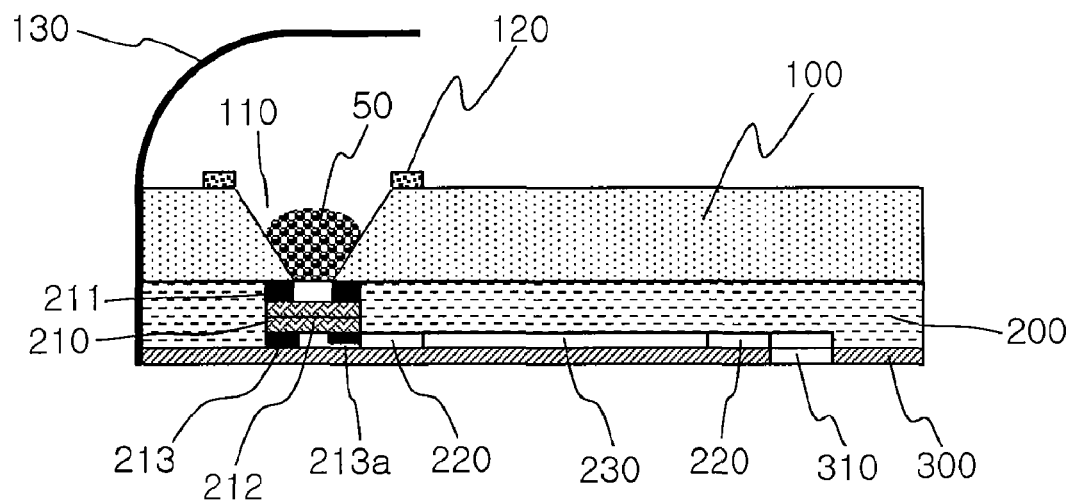
FIG. 2 is a cross-sectional view illustrating the filtration device for separating blood plasma illustrated in FIG. 1 taken along line X-X' of FIG. 1.

FIG. 1 is a perspective exploded view for explaining a structure of a filtration device for the separation of blood plasma according to an embodiment of the present invention. FIG. 2 is a cross-sectional view illustrating the filtration device for the separation of blood plasma illustrated in FIG. 1 taken along line X-X'.

Referring to FIGS. 1 and 2, the filtration device for the separation of blood plasma according to the present invention has a structure in which a substrate 100 including a blood inlet, a substrate 200 including a filtering unit for filtering blood flowing though the blood inlet to separate blood plasma, and a substrate 300 including an air outlet. For the convenience of description, the three substrates 100, 200, and 300 are called as an upper substrate, an intermediate substrate, a lower substrate, respectively.

The blood inlet 110 is formed by penetrating the upper substrate 100 in a direction of a thickness of the upper substrate 100. In addition, the upper substrate 100 further includes a double sided adhesive tape 120 adhered to an upper surface of the upper substrate 100 to surround the blood inlet 110 in a shape of a closed curve as a sealing means for disabling blood flowing through the blood inlet 110 from flowing out, and an cover film 130 which is to be adhered to the upper surface of the upper substrate 100 by the double sided adhesive tape 120 to seal the blood inlet 110.

The filtering unit is formed by perforating the intermediate substrate 200 in a direction of a thickness of the intermediate substrate 200 at a position facing the blood inlet 110. The filtering unit includes filters 212 for filtering blood cells out and passing only blood plasma, a filter chamber 210 in which elastic plates 211 and 213 are stacked to prevent blood from unnecessarily flowing out, a microchannel 220 that the blood plasma passing through the filters 212 fills, and a microchamber 230. The lower elastic plate 213 of the two elastic plates 211 and 213 of the filter chamber 210 contacts the lower substrate 300 and has an opening portion 213a so as to enable the extracted blood plasma to flow into the microchannel 220.

The air outlet 310 is formed by penetrating the lower substrate 300 in a direction of a thickness of the lower substrate 300 at a position connected to the microchannel 220 connected to an outlet of the microchamber 230.

In order to operate the filtration device having the aforementioned structure, blood 50 is injected through the blood inlet 110, the blood inlet 110 is sealed by the double sided adhesive tape 120 and the cover film 130, and the cover film 130 is pressed. Then, blood cells in the blood 50 are removed while the blood 50 is filtered by the filters 212, and blood plasma passing through the filters 212 fills the microchamber 230 through the microchannel 220. Through the air outlet 310, air is exhausted for promoting the flow of blood plasma.

The filtration device according to the present invention may further include antigens, antibodies, enzymes, micro/nano particles, electrodes, sensors, and the like so that biological reactions and detections with the blood plasma filling the microchamber 230 occur.

The filters 212 may be formed by a paper, a glass fiber, or a porous medium or formed in a single-layered or a multi-layered structure.

A thickness of the filter chamber 210 may be less than the sum of thicknesses of the filters 212 and the elastic plates 211 and 213 so that the filters 212 and the elastic plates 211 and 213 can be pressed in the filter chamber 210 by the adhered upper, intermediate, and lower substrates 100, 200, and 300. In addition, an internal shape and an internal size of the filter chamber 210 may be the same as the shape and the size of the filters 212, respectively.

In addition, the elastic plates 211 and 213 have a shape of O to prevent blood from flowing out trough an interface between the upper and intermediate substrates 100 and 200. The elastic plates 211 and 213 are adhered to the upper, intermediate, and lower substrates 100, 200, and 300 and cross-sections of the elastic plates 211 and 213 may be equal to or larger than the cross-section of the filter chamber 210.

Figure 3A:
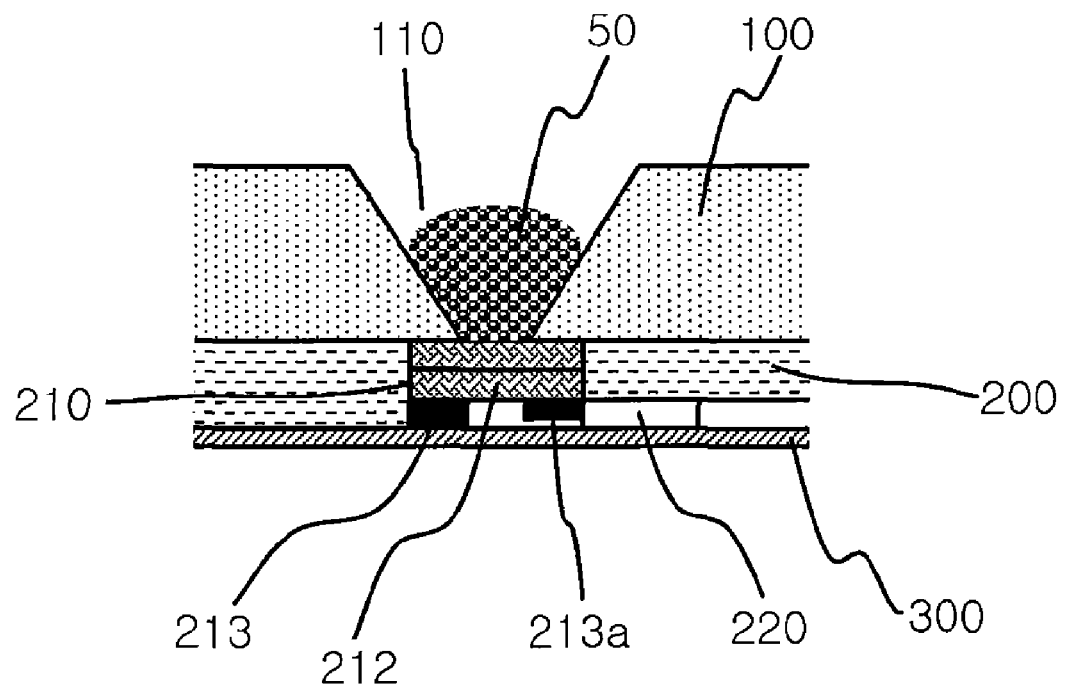
FIGS. 3A and 3B are views for explaining modifications of a filter-stacked structure illustrated in FIG. 2.
Figure 3B:
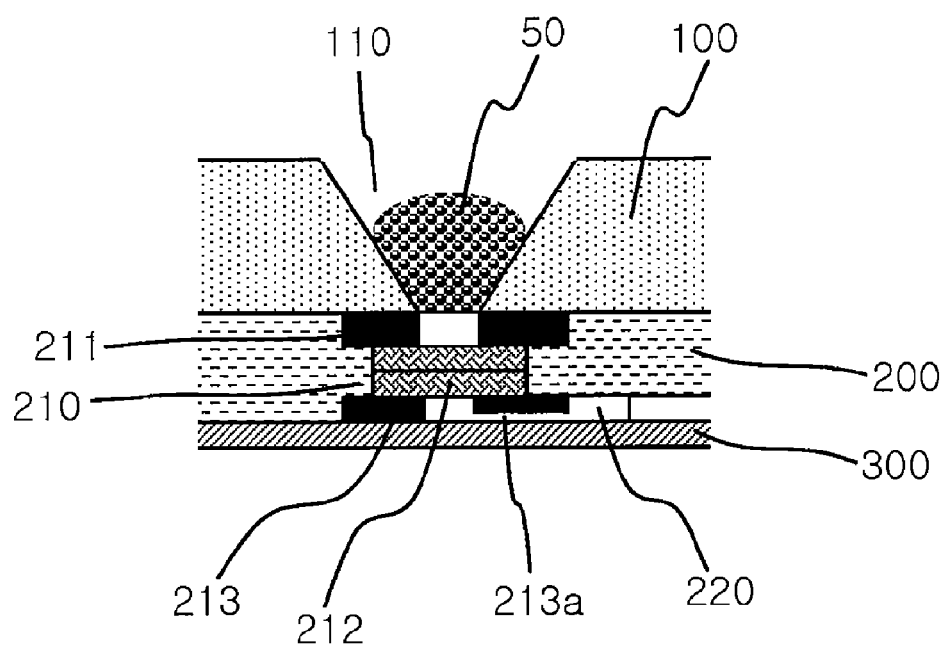

FIGS. 3A and 3B are views for explaining modifications of the structure of the filter chamber 210. As illustrated in FIG. 3A, the filter chamber 210 may include only the filter 212 and the lower elastic plate 213. Otherwise, as illustrated in FIG. 3B, the filter chamber 210 may include the upper elastic plate 211, the filters 212, and the lower elastic plate 213. In addition, as illustrated in FIG. 3B, the filter chamber 210 according to the present invention may be formed so that sizes of the elastic plates 211 and 213 are larger than that of the filters 212. In the structure as illustrated in FIG. 3B, flows of the blood 50 in a direction of a side surface may be reduced. However, in this case, a more complex shape is used for the filter chamber 210.

In addition, the lower elastic plate 213 may include the opening portion 213a formed by cutting a portion of the lower elastic plate 213 connected to the microchannel 220 so as to enable the blood plasma extracted by the filter 212 to flow into the microchannel 220 properly. Here, the cut portion may have such a shape that the blood plasma can properly flow into the microchannel 220.

Figure 4A:
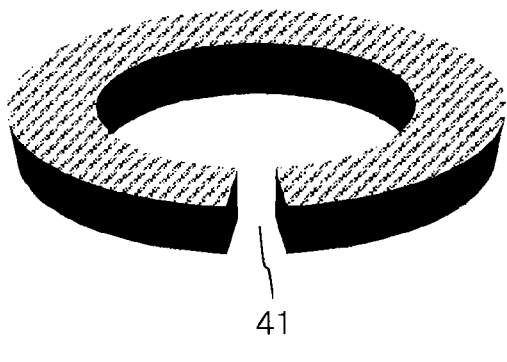
FIGS. 4A and 4B are views for explaining a detailed shape of an elastic plate illustrated in FIG. 1.
Figure 4B:
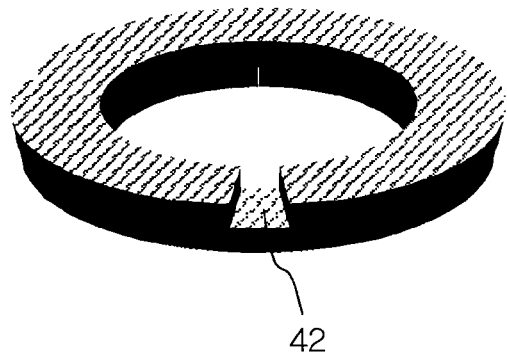

FIGS. 4A and 4B are views for explaining a detailed shape of the lower elastic plate 213. The lower elastic plate 213 illustrated in FIG. 4A has an opening portion 41 formed by cutting the plate 213, and the lower elastic plate 213 illustrated in FIG. 4B has an opening portion 42 formed by cutting a portion of the plate 213 so that the portion has a step height. Through the opening portion 41 or 42 of the lower elastic plate 213 having the aforementioned shapes, the blood plasma extracted by the filter 212 can flow into the microchannel 220.

Next, the shape of the portion of the blood inlet 110 contacting the intermediate substrate 200 may be the same as the internal shape of the filter chamber 210, particularly, an internal shape formed by perforating the upper elastic plate 211. For example, the shape may be a circle having a diameter ranging from 2 to 5 mm.

In addition, the blood inlet 110 may have such a size that blood of about from 10 uL to 200 uL can be inserted to be used for a disposable biochip. More specifically, an upper portion of the blood inlet 110 may have a circular shape having a diameter of about from 5 to 15 mm so as to be easily pressed by a finger. According to the current embodiment, the blood inlet 110 has a cylindrical shape in which an area of the upper portion is larger than that of a lower portion.

In addition, a volume of the microchamber 230 formed at the intermediate substrate 200 may be 50% of a volume of the blood inlet 110 or less. This is because the maximum volume of blood plasma that can be separated from the injected blood is 52 to 57% of a volume of the injected blood.

In addition, the cover film 130 may be made of a material that can be deformed when pressed and maintain the deformed shape after the pressing is removed. For example, the material may be a thin polymer film.

In addition, the double sided adhesive tape 120 may be formed in a shape of a closed curve at an upper boundary of the blood inlet 110 and completely sealed by the adhered cover film 130 and upper substrate 100. According to the current embodiment, only the double sided adhesive tape 120 is exemplified. However, according to the present invention, the double sided adhesive tape 120 may be replaced with another sealing means for simply sealing the blood inlet 110.

The upper, intermediate, and lower substrates 100, 200, and 300 including the blood inlet, the filtering unit, and the air outlet, respectively, may be made of a material selected from the group consisting of a plastic, a silicon, a rubber, and a glass and preferably may be made of a plastic which is cheap and can be applied to a disposable biochip.

The plastic implemented as the substrates 100, 200, and 300 may be made of a material selected from the group consisting of poly-dimethyl siloxane (PDMS), polymethylmethacrylate (PMMA), polycarbonate (PC), cycloolefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutylene-terephthalate (PBT), fluorinated ethylenepropylene (FEP), and perfluoralkoxyalkane (PFA).

In addition, the upper, intermediate, and lower substrates 100, 200, and 300 may be manufactured in various methods according to materials and for example, may be formed by using one or more selected from hot embossing, injection molding, numerical control (NC) machining, laser ablation, arc-discharging, casting, stereolithography, rapid prototyping, and photolithography. Particularly, when the substrates 100, 200, and 300 are made of plastic so as to be applied to the cheap disposable biochip, the hot embossing or the injection molding may be used.

In addition, the upper, intermediate, and lower substrates 100, 200, 300 may be adhered in various methods according to materials of the substrates 100, 200, and 300. For example, one or more selected from thermal bonding, epoxy bonding, chemical bonding, ultrasonic bonding, and plasma bonding may be used.

The filtration device for the separation of blood plasma according to the present invention has a stacked structure and can be integrated into a biochip to be directly applied. In addition, the filtration device has a simple structure that can be simply manufactured and requires low costs, so that the filtration device is appropriate for disposable uses. Particularly, the filtration device according to the present invention can separate blood plasma with a simple manipulation of injecting a small amount of blood and pressing the filter device for separating blood plasma without a driving unit.

In addition, the filtration device according to the present invention includes the filtering unit and the elastic plates that are stacked, so that leaking of blood cells can be minimized, and blood plasma separation efficiency can be increased. As a result, a need for a biochip to separate blood plasma effectively and rapidly from a small amount of blood can be satisfied.

In addition, the filtration device according to the present invention can be manufactured by using a plastic that is cheap, so that the filtration device can be applied to a disposable biochip for detecting a specific disease from blood.

While the present invention has been shown and described in connection with the exemplary embodiments, it will be apparent to those skilled in the art that modifications and variations can be made without departing from the spirit and scope of the invention as defined by the appended claims.

What is claimed is:

1. A disposable multi-layered filtration device for the separation of blood plasma, comprising:
   an upper substrate including a blood inlet;
   an intermediate substrate including a filtering unit for extracting blood plasma from blood flowing through the blood inlet; and
   a lower substrate including an air outlet,
   wherein the upper substrate, the intermediate substrate, and the lower substrate are stacked and adhered, and
   wherein the filtering unit comprises:
      a filter chamber which is formed by perforating the intermediate substrate in a direction of a thickness of the intermediate substrate at a position facing the blood inlet and includes one or more filters for filtering the blood flowing from the blood inlet to pass only the blood plasma;
      a microchamber that the blood plasma extracted by the filters of the filter chamber fills; and
      a microchannel connecting the filter chamber to the microchamber.

2. The device of claim 1, wherein the filters are made of a paper, a glass fiber, or a porous material.

3. The device of claim 1, wherein the microchamber further includes one or more of antigens, antibodies, enzymes, micro/nano particles, electrodes, and sensors for generating biological reactions and detections with the blood plasma filling the microchamber.

4. The device of claim 1, wherein the filter chamber further includes a lower elastic plate which is disposed at a lower portion of the filter, has a shape of O, and has an opening portion for enabling the blood plasma to flow into the microchannel.

5. The device of claim 4, wherein the filter chamber further includes an upper elastic plate which is disposed at an upper portion of the filter and has the shape of O.

6. The device of claim 5, wherein the blood inlet is formed by perforating the upper substrate in a direction of a thickness of the upper substrate, and a portion of the blood inlet contacting the intermediate substrate has a shape the same as an internal shape of the upper elastic plate.

7. The device of claim 5, further comprising an adhesive means and a cover film for sealing the blood inlet.

8. The device of claim 5, wherein a thickness of the filter chamber is equal to or less than the sum of thicknesses of the filters and the upper and lower elastic plates so that the filter and the upper and lower elastic plates are pressed in the filter chamber by the adhered upper, intermediate, and lower substrates.

9. The device of claim 5, wherein cross-sections of the upper and lower elastic plates are equal to or larger than a cross-section of the filter chamber.

10. The device of claim 6, wherein the blood inlet has such a size that blood of about from 10 uL to 200 uL is inserted.

11. The device of claim 7, wherein the cover film is made of a thin polymer film so that the cover film is deformed when pressed and maintains the deformed shape after the pressing is removed.

12. The device of claim 7, wherein the adhesive means is a double sided adhesive tape formed in a shape of a closed curve at an upper boundary of the blood inlet so as to be adhered to the cover film and the upper substrate.

13. The device of claim 1, wherein the upper, intermediate, and lower substrates are made of a material selected from the group consisting of poly-dimethyl siloxane (PDMS), polymethylmethacrylate (PMMA), polycarbonate (PC), cycloolefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinyl chloride (PVC), polyvinylidene fluoride (PVDF), polybutyleneterephthalate (PBT), fluorinated ethylenepropylene (FEP), and perfluoralkoxyalkane (PFA).

14. The device of claim 1, wherein the upper, intermediate, and lower substrates are adhered by using one selected from thermal bonding I epoxy bonding, chemical bonding, ultrasonic bonding, and plasma bonding.

* * * * *